US008615379B2

(12) United States Patent
Li et al.

(10) Patent No.: US 8,615,379 B2
(45) Date of Patent: Dec. 24, 2013

(54) METHOD FOR MUTLI-STAGE SPATIAL SAMPLING WITH MULTIPLE CRITERIA

(75) Inventors: Ke Betty Li, Moon Township, PA (US); Linda M. Abriola, Beverly, MA (US)

(73) Assignee: Tufts University, Medford, MA (US)

( * ) Notice: Subject to any disclaimer, the term of this patent is extended or adjusted under 35 U.S.C. 154(b) by 468 days.

(21) Appl. No.: 12/518,333

(22) PCT Filed: Dec. 11, 2007

(86) PCT No.: PCT/US2007/025440
§ 371 (c)(1),
(2), (4) Date: Apr. 23, 2010

(87) PCT Pub. No.: WO2008/073475
PCT Pub. Date: Jun. 19, 2008

(65) Prior Publication Data
US 2010/0211357 A1    Aug. 19, 2010

Related U.S. Application Data

(60) Provisional application No. 60/874,214, filed on Dec. 11, 2006.

(51) Int. Cl.
*G06F 17/18*     (2006.01)
*G06F 19/00*     (2011.01)
*E02B 13/00*     (2006.01)

(52) U.S. Cl.
USPC ........................................... 702/181; 405/52

(58) Field of Classification Search
USPC ........................................... 702/181; 405/52
See application file for complete search history.

(56) References Cited

U.S. PATENT DOCUMENTS

| | | | | |
|---|---|---|---|---|
| 5,243,686 A | * | 9/1993 | Tokuda et al. | 704/200 |
| 5,468,088 A | * | 11/1995 | Shoemaker et al. | 166/245 |
| 5,646,863 A | | 7/1997 | Morton | |
| 5,813,798 A | * | 9/1998 | Whiffen | 405/52 |
| 7,031,838 B1 | | 4/2006 | Young et al. | |
| 2005/0177309 A1 | | 8/2005 | Sri Ranjan et al. | |
| 2006/0047613 A1 | * | 3/2006 | Labreuche | 706/46 |

OTHER PUBLICATIONS

PCT International Search Report; Corresponding PCT International Patent Application Serial No. PCT/US2007/025440; Applicant: Tufts University; Filed Dec. 11, 2007, (2 pgs.).
Abriola et al., (2005) "Pilot-scale demonstration of surfactant-enhanced PCE solubilization at the Bachman road site. 1. Site characterization and test design" Environ. Sci. Technol;. 31:1778-1790.
Abriola, (2005) "Contaminant source zones: remediation or perpetual stewardship?" Env. Health Pers.; 113: A438-A439.
Almeida et al., (1994), "Joint simulation of multiple variables with a Markov-type coregionalization model." Math. Geol.; 26: 565-588.

(Continued)

*Primary Examiner* — Alexander H Taningco
*Assistant Examiner* — Manuel Rivera Vargas
(74) *Attorney, Agent, or Firm* — Tanya A. Arenson; Casimir Jones, S.C.

(57) ABSTRACT

The present invention provides a method for implementing a multi-stage spatial sampling strategy to select optimal sampling locations and determine an optimal sampling density for a quantification of mass discharge uncertainty in a field. The present invention also provides systems and methods for estimating probability of a mass discharge in a control plane.

9 Claims, 15 Drawing Sheets

(56) References Cited

OTHER PUBLICATIONS

Bogardi et al., (1985) "Multicriterion Network Design Using Geostatistics." Water Resourc. Res.; 21: 199-208.

Bueso et al., (1998) "A state-space model approach to optimum spatial sampling design based on entropy." Env. Eco Stat.; 5: 29-44.

Christ et al., (2005) "Comparison of two-dimensional and three-dimensional simulations of dense nonaqueous phase liquids (DNAPLs): Migration and entrapment in a nonuniform permeability field." Water Resour Res.; 41: W01007.

Christ et al., (2006) "Estimating mass discharge from dense nonaqueous phase liquid source zones using upscaled mass transfer coefficients: an evaluation using multiphase numerical simulations." Water Resource Res; 42:W11420.

Christakos et al., (1992) "Sampling design for spatially distributed hydrogeologic and environmental processes." Adv. Water Res. 15: 219-237.

Christakos et al., (1993) "Sampling design for classifying contaminant level using annealing search algorithms." Water Resourc. Res.; 29: 4063-4076.

Cieniawski et al., (1995) "Using Genetic Algorithms to Solve a Multiobjective Groundwater Monitoring Problem." Water Resourc. Res. 31: 399-409.

Deutsch, (1997) "Direct assessment of local accuracy and precision" Geostatistics Wollongong; 1 and 2(8), 115-125.

Doughtery et al., (1991) "Optimal Groundwater Management: 1. Simulated Annealing." Water Resourc. Res.; 27: 2493-2508.

Dungan et al., (1998) "Spatial prediction of vegetation quantities using ground and image data" Int. J. Remote Sens.; 19:267-285.

Feenstra et al., (1996) "Conceptual models for the behavior of dense non-aqueous phase liquids (DNAPLs) in the subsurface", Dense chlorinated solvents and other DNAPLs in groundwater; history, behavior, and remediation; Waterloo Press, Portland, OR, United States, USA.

Freeze et al., (1997) "A Framework for Assessing Risk Reduction Due to DNAPL Mass Removal from Low-Permeability Soils." Ground Water; 35: 111-123.

Gomez-Hernandez et al., (1990), "ISIM3D—An ANSI-C three-dimensional multiple indicator conditional simulation program." Comput. Geosci.; 16: 395-440.

Gomez-Hernandez et al., (1993), "Joint sequential simulation of multigaussian fields." Geostat. Troia; 92,1 and 2 (5): 85-94.

Hatfield et al., (2004) "A direct passive method for measuring water and contaminant fluxes in porous media." J. Cont. Hydro;. 75: 155-181.

Interstate Technology & Regulatory Council, 2004 Strategies for Monitoring the Performance of DNAPL Source Zone Remedies.

Jarsjo et al., (2005) "Monitoring groundwater contamination and delineating source zones at industrial sites: uncertainty analyses using integral pumping tests." J. Cont. Hydro.; 79: 107-134.

Journel, (1983), "Nonparametric Estimation of Spatial Distributions," Intl Assoc. Math Geol 15: 445-468.

Ko et al., (1995) "An Exact Algorithm for Maximum Entropy Sampling." Oper Res.; 43: 684-691.

Lemke et al., (2004) "Dense nonaqueous phase liquid (DNAPL) source zone characterization: Influence of hydraulic property correlation on predictions of DNAPL infiltration and entrapment." Water Resource Res.; 40: W01511.

Mao et al., (1999) "Conditional 3D simulation of lithofacies with 2D seismic data" Comput. Geosci.; 25: 845-862.

McBratney et al., (1981) "The design of optimal sampling schemes for local estimation and mapping of regionalized variables—I: Theory and method." Comp & Geosci.; 7: 331-334.

Meyer et al., (1994) "Monitoring network design to provide initial detection of groundwater contamination." Water Resourc. Res;. 30: 2647-2659.

Nunes et al, 2004, "Groundwater Monitoring Network Optimization with Redundancy Reduction." J. Water Resourc. Plan, Manage-ASCE; 130: 33-43.

Painter et al., (2001) "Flexible scaling model for use in random field simulation of hydraulic conductivity" Water Resour. Res., 37,:1155-1163.

Parker et al., (2004) "Modeling field-scale dense nonaqueous phase liquid dissolution kinetics in heterogeneous aquifers." Water Resour.; 40.

Rao et al., (2002) "Technology integration for contaminated site remediation; clean-up goals and performance criteria." Groundwater quality; natural and enhanced restoration of groundwater pollution, IAHS-AISH Publ., 275: 571-578.

Saito, (2002), "Accounting for measurement error in uncertainty modeling and decision-making using indicator kriging and p-field simulation: application to a dioxin contaminated site" Environmetrics; 13: 555-567.

Savic et al., (1997) "Genetic algorithms for Least-cost design of water distribution networks." J water Resourc. Plan Manag ASCE 123: 67-77.

Shieh et al., (2005) "An interactive sampling strategy based on information analysis and ordinary kriging for locating hot spot regions." Math Geo;. 37: 29-48.

Soga et al., (2004), "A review of NAPL source zone remediation efficiency and the mass flux approach" J. Hazard. Mater.; 110,13-27.

Stroo et al., (2003) "Remediating chlorinated solvent source zones." Env. Sci Tech; 37: 224A-230A.

Van Groenigen et al., (1998) "Constrained optimization of spatial sampling using continuous simulated annealing." J. Env. Quality; 27: 1078-1086.

Van Groenigen et al., (1999) "Constrained optimisation of soil sampling for minimisation of the kriging variance." Geoderma 87,239-259.

Van Groenigen et al., (2000) "The influence of variogram parameters on optimal sampling schemes for mapping by kriging." Geoderma; 97: 223-236.

Verly, (1993) "Sequential Gaussian cosimulation—A simulation method integrating several types of information" Geostatistics Troia; 92:1 and 2(5), 543-554.

Warrick et al., (1987) "Optimization of Sampling Locations for Variogram Calculations." Water Resource Res. 23: 496-500.

Watson et al., (1995), "Infill Sampling Criteria to Locate Extreme," Math Geo 27: 589-608.

Yao et al., (2000) "Integration of seismic attribute map into 3D facies modeling" J. Pet. Sci. Eng.; 27:69-84.

Yfantis et al., (1987) "Efficiency of kriging estimation for square, triangular, and hexagonal grids." Math Geo; 19: 183-205.

Zeru et al., (2005) "Analysis of groundwater contamination using concentration-time series recorded during an integral pumping test: bias introduced by strong concentration gradients within the plume." J. Cont. Hyrol 81: 106-124.

\* cited by examiner (a)

(b)

(c)

(d)

(a)

(b)

(c)

(d)

(a)

(b)

(c)

(d)

(a)

(b)

(c)

(d)

METHOD FOR MUTLI-STAGE SPATIAL SAMPLING WITH MULTIPLE CRITERIA

The present application claims priority to U.S. Provisional Application No. 60/874,214 filed Dec. 11, 2006, incorporated herein by reference in its entirety.

This invention was made with government support under contract W912HQ-04-C-0006 awarded by the U.S. Army Corps of Engineers, Humphreys Center Support Activity. The government has certain rights in the invention.

FIELD OF THE INVENTION

The present invention provides a method for implementing a multi-stage spatial sampling strategy to select optimal sampling locations and determine an optimal sampling density for a quantification of mass discharge uncertainty in a field. The present invention also provides systems and methods for estimating probability of a mass discharge in a control plane.

BACKGROUND OF THE INVENTION

Contaminant mass discharge across a control plane downstream of a Dense Nonaqueous Phase Liquid (DNAPL) source zone has great potential to serve as a metric for the assessment of the effectiveness of source zone treatment technologies and for the development of risk-based source-plume remediation strategies. However, field estimated mass discharge is always subject to great uncertainty arising from non-exclusive sampling. The accuracy of the mass discharge estimate and the magnitude of its quantifiable uncertainty depend upon the amount of information provided by the sample data.

The difficulties encountered in the remediation of DNAPL in the subsurface have instigated numerous researches in the benefits evaluation of DNAPL source zone depletion. Mass discharge, defined as the contaminant mass per unit time ($[M/T]$) migrating across a hypothetic control plane orthogonal to the mean groundwater flow, has been widely proposed as a potential metric to assess the impact of partial mass removal in DNAPL source zones (Interstate Technology & Regulatory Council, 2004, Strategies for Monitoring the Performance of DNAPL Source Zone Remedies; Soga et al., 2004, J. Haz. Mat. 110:13-26; Rao et al., 2002, Groundwater Quality 2001 Conference, Sheffield, UK, 275:571-578; Freeze and McWhorter, 1997, Ground Water 35:111-123; Feenstra et al., 1996, in Dense Chlorinated Solvents and Other DNAPLs in Groundwater, Waterloo Press, USA).

In the field, mass discharge prediction made from relative observations such as contaminant concentration, hydraulic conductivity, or mass flux ($[M/T \cdot L^2]$) is always subject to uncertainty (Jarsjo et al., 2005, J. Cont. Hydro. 79:107-134; Zeru and Schafer, 2005, J. Cont. Hyro. 81:106-124; Hatfield et al., 2004, J. Cont. Hydro. 75:155-181), however, the uncertainty is typically not quantified. This circumstance makes the implementation of mass discharge as an assessment metric extremely difficult (Stroo et al., 2003, Env. Sci. Tech. 37:224A-230A) since any decision regarding site management or benefits/cost evaluation using incomplete information is unreliable (Abriola, 2005, Env. Health Pers. 113: A438-A439). A geostatistical approach has been proposed to quantify the uncertainty of mass discharge using multi-level measurements of contaminant concentration and hydraulic conductivity. The fully characterized uncertainty, in terms of the probability distribution of mass discharge, is ready to serve risk-based source-plume remediation strategies. Unfortunately, implementation of this geostatistical approach on numerically simulated control planes (Christ et al., 2005, Water Resour. Res. 41:W01007; Christ et al., 2006, Water Resourc. Res. in press; Lemke et al., 2004, Water Resourc. Res. 40:W01511) suggests that the sampling density, defined as the proportion of the sampled area to the whole control plane, could be as high as 6~7% to achieve an accurate model of uncertainty for the control planes with scattered small hot spots and large areas of near-zero concentration. This conclusion was made for the one stage sampling design with a regular sampling pattern (rectangular). The requirement of such a high sampling density is mainly due to the limitation of the geostatistical approach on non-representative samples.

Classical sampling techniques (Cochran, 1977, Sampling Techniques, John Wiley & Sons, Inc., New York, N.Y., pp. 428) typically offer limited help for sampling design when spatially distributed processes are encountered. Instead, geostatistics is usually employed for spatial sampling design (Thompson, 2002, Sampling, $2^{nd}$ Ed. John Wiley & Sones, Inc., New York, N.Y., pp. 367; Isaaks and Srivastava, 1989, Applied Geostatistics, Oxford Univ. Press, New Tork, N.Y., pp. 561; Goovaerts and Journel, 1997, Geostatistics for Natural Resource Evaluation, Oxford Univ. Press, New York, N.Y.). The term spatial sampling design refers to the procedure that decides the arrangement of observations (e.g. sampling density and sampling locations) for specific purposes (Christakos and Olea, 1992, Adv. Water Res. 15:219-237). Different purposes result in different selection/formulation of sampling criteria, and thus lead to different sampling design.

One of the popular sampling criteria is the minimization of kriging variance (variance of kriging error), because kriging variance is independent of data values, only depending on the data configuration and the covariance structure. McBratney et al. (1981, Comp. & Geosci. 7:331-334) used this criterion to optimize the spacing of a sampling grid, given an a priori semivariogram exists. van Groenigen (2000, Geoderma 97:223-236) further discussed the impacts of the optimization criteria (minimization of mean kriging variance versus maximum kriging variance), semivariogram model type, and semivariogram model parameters. This criterion directly deals with the kriging error, which is closely corrected to the quality of the prediction of geostatistical method (kriging). The advantage of this method is that kriging variance by definition is independent of data values, so it is possible to be computed in advance of real sampling. However, the independency of data values also adversely impacts this criterion. For example, two locations with different contrast in the surrounding data values could have the same kriging variance, given the same data configuration (Goovaerts and Journel, 1997). Also, sampling cannot be preferentially guided in the region with high/low values.

This criterion is also very sensitive at the boundary of the study domain. The covariance matrix (or the semivariogram model) has to been known a priori, which is another disadvantage. Another type of criteria indirectly improves the results of geostatistical prediction by improving the quality of the information contained in sample data. For example, with no information to infer a reliable semivariogram in advance, van Groenigen and Stein (1998, J. Env. Quality 27:1078-1086) proposed to incorporate two sampling criteria: (1) the Minimization of the Mean of Shortest Distances Criterion (MMSD), and (2) The WM criterion, a criterion proposed by Warrick and Myers (1987, Water. Resourc. Res. 23:496-500). The MMSD criterion is for the coverage of the entire study area, which requires all observations spread evenly over the study area. The WM criterion is for the inference of a reliable semivariogram, which optimizes the distribution of observation pairs over different lag distances to an ideal distribution for the computation of an experimental semivariogram. The WM criterion is a complement to the MMSD criterion (but conflicting), because a sampling design with only MMSD will likely cause very few observation pairs for short lag distances and thus yield poor experimental semivariograms, especially with a limited number of observations.

Another example of this type of criterion is the study of Yfantis et al. (1987, Math. Geo. 19:183-205), which compared the performance of different sampling patterns on the computation of experimental semivariograms. By managing the quality of the information transmitted by observations for geostatistics, the ultimate purpose of this type of criteria is still to obtain reliable predictions from geostatistical techniques. The various natures of spatial surveys could yield other sampling purposes, thus different sampling criteria (Watson and Barnes, 1995, Math. Geo. 27:589-608; Christakos and Killam, 1993, Water Resourc. Res. 29:4063-4076; (Bogardi et al., 1985; Christakos and Olea, 1988, Adv. Water Res. 15:219-237; Ko et al., 1995, Oper. Res. 43:684-691; Bueso et al., 1998, Env. Eco. Stat. 5:29-44).

Once sampling criteria are appropriately selected, the remaining problem is the search for the optimal sampling locations. Most researchers treat this problem as an optimization problem. Sampling criteria are formulated in the objective function (fitness function), which is usually a function of coordinates (van Groenigen and Stein, 1998), or a function of grid spacing (thus sampling density) (Bogardi et al., 1985, Water Resourc. Res. 21:199-208). Various optimization algorithms have been used for the search, such as the simulated annealing algorithm (Dougherty and Marryott, 1991, Water Resourc. Res. 27:2493-2508; Christakos and Killam, 1993; van Groenigen et al., 1999, Geoderma 87:239-259) and the genetic algorithm (Cieniawski et al., 1995, Water Resourc. Res. 31:399-409; Savic and Walters, 1997, J. Water Resourc. Plan. Manag.—ASCE 123:67-77). However, two difficulties remained in this type of formulation. First, the quantities in the objective function should be able to be measured or computed before real sampling occurs, which limits the selection of sampling criteria. Second, the sampling density or sampling pattern should be known in advance. In case that sampling density is known, then the sampling locations are optimized. If sampling pattern has been decided, the optimization is for the sampling density (grid spacing). Moreover, it is common to include multiple sampling criteria and the objective function is usually the weighted average of these criteria. However, the weights are usually decided arbitrarily in advance. For example, equal weights are commonly used after each item in the objective function and are appropriately scaled (Nunes et al., 2004, J. Water Resourc. Plan. Manag.—ASCE 130:33-43). More advanced combinations of different weights are used to discuss the trade-off of each criterion (Bogardi et al., 1985; Meyer et al., 1994, Water Resourc. Res. 30:2647-2659; Cieniawski et al., 1995).

Another method is to implicitly perform a multi-stage sampling, where each stage has different pre-set weights and the sampling stages are decided according to a pre-set "cooling" schedule (Shieh et al., 2005, Math. Geo. 37:29-48).

In view of the above, what is needed is a sampling design that enables the selection of optimal sampling locations and that determines the minimal sampling density for an accurate quantification of mass discharge uncertainty in a field.

SUMMARY OF THE INVENTION

The present invention provides a method for implementing a multi-stage spatial sampling strategy to select optimal sampling locations and determine an optimal sampling density for a quantification of mass discharge uncertainty in a field. The present invention also provides systems and methods for estimating probability of a mass discharge in a control plane.

A multi-stage spatial sampling strategy is described herein for the selection of optimal sampling locations and the determination of the minimal sampling density for an accurate quantification of mass discharge uncertainty in a field. Two sampling criteria are incorporated to ensure coverage of the entire control plane and the delineation of highly concentrated areas (hot spots). In some embodiments, the Multiple Criteria Decision Making (MCDM) theory is used to form a solution for locating additional observations and to assign weights for the two sampling criteria according to the information importance of each criterion. Application of this methodology to numerically simulated transects demonstrates that the sampling strategy as defined herein yields a 50% reduction in sampling density in comparison to one stage sampling. An interactive computer program provided by the invention provides use in real-time to guide field sampling progress for mass discharge estimation.

The two sampling criteria are adapted to indirectly deal with the geostatistical prediction by improving the spatial pattern recognition through observations; the delineation of highly concentrated area (hot spots) and the coverage of the entire domain. The first criterion, the delineation of hot spots, is not computed or measured in advance of real sampling. Therefore, the sampling design problem is formulated as a decision making problem. The Multiple Criteria Decision Making (MCDM) theory (Zeleny, 1982, Multiple Criteria Decision Making, McGraw-Hill Book Co., New York N.Y.) is adapted to form a compromise solution for the selection of sampling locations. The formulation makes the work different from other researches in that; (1) neither the sampling density nor the sampling pattern is decided a priori, instead the minimal sampling density is determined by the accuracy of the uncertainty model of mass discharge and there is no pre-set sampling pattern, (2) more freedom is allowed in the selection of sampling criteria in that there is no requirement that the sample criteria should be mathematically formulated in terms of quantities that can be measured or computed in advance of real sampling and, (3) the weights for sampling criteria are objectively determined and automatically updated by data themselves, specifically by the information importance of each sampling criterion.

The computational processes of the invention may be designed into software or into memory of a computer device. This software is loaded into a computer or computational device that is easily transported on site to a field where needed, thereby allowing for real time determination of sampling locations and delineation of hot spots in a contamination field.

In one embodiment, the present invention provides a method for selecting optimal sampling locations for mass discharge analysis comprising obtaining initial measurements of contaminant concentration and hydraulic conductivity from a sampling, generating a probability distribution of mass discharge using said measurements, estimating variance of contaminant concentration and local sampling density from said measurements, calculating weights for said variance and local sampling density, selecting a different sampling location using said variance, local sampling density and weights, obtaining additional measurements from said different sampling location, and updating said probability distribution using said additional measurements. In some embodiments, the preceding method is repeated more than once. In some embodiments, said calculating comprises computing information importance measured by information entropy. In some embodiments, said selecting comprises composite programming in multi-criterion decision making.

In one embodiment, the present invention provides systems and methods for estimating probability distribution of a mass discharge within a control plane. Systems for conducting such a method may comprise a processor configured to obtain measurements of contaminant concentration and hydraulic conductivity from a sampling, modeling of conditional probability distributions of contamination concentration and hydraulic conductivity by separately interpolating said measurements of contaminant concentration and hydraulic conductivity at a plurality of locations within said control plane, creating realizations of spatial distributions of contaminant concentration and hydraulic conductivity using said conditional probability distribution, generating realizations of spatial distribution of local mass flux within said control plane using said created realizations, and estimating a probability distribution of mass discharge of said control plane using said generated realizations. In some embodiments, said modeling comprises conducting indicator kriging to interpolated contaminant concentration and hydraulic conductivity. In some embodiments, said creating comprises a co-simulation of contaminant concentration and hydraulic conductivity using p-field simulation. In some embodiments, said generating comprises a variance estimation of contaminant concentration and hydraulic conductivity using said realizations.

DETAILED DESCRIPTION OF THE INVENTION

Figure 1:
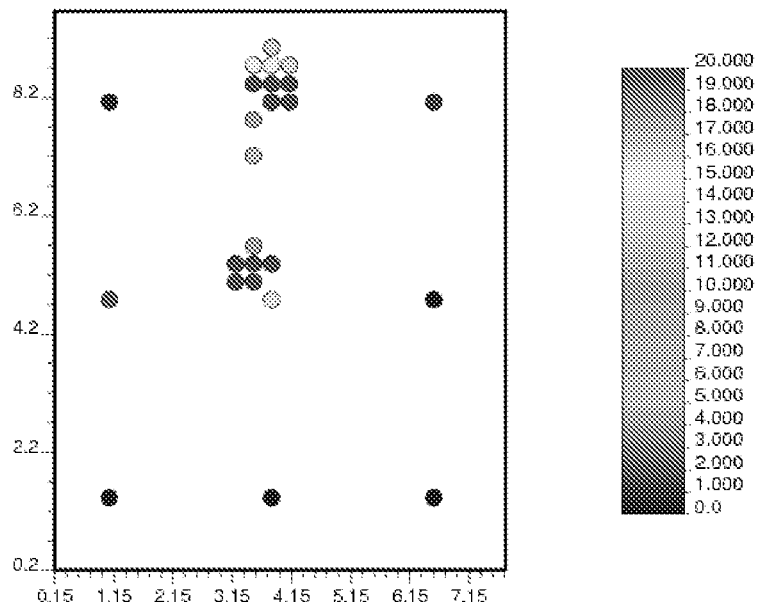
FIG. 1 shows an example of the multi-stage sampling locations according to simulated value (a): 25 observations (b) 45 observations (c) 208 observations (d) reference field.
Figure 1:
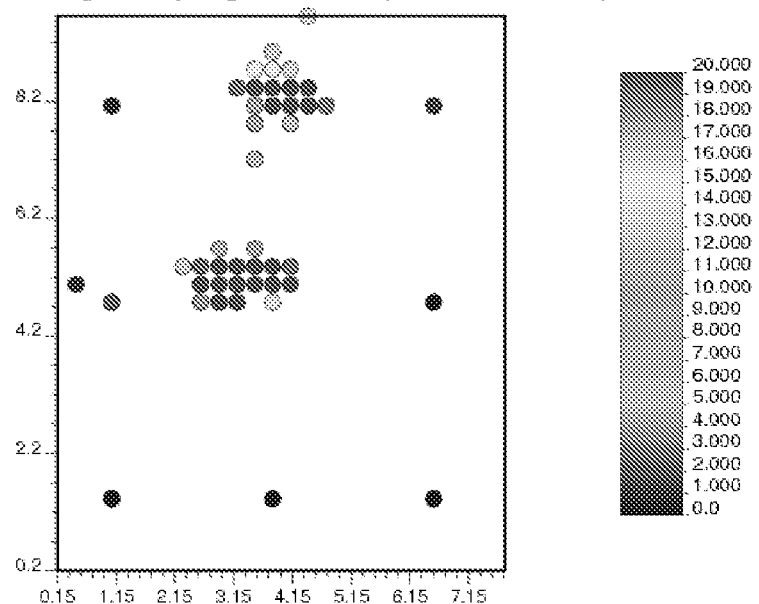
Figure 1:
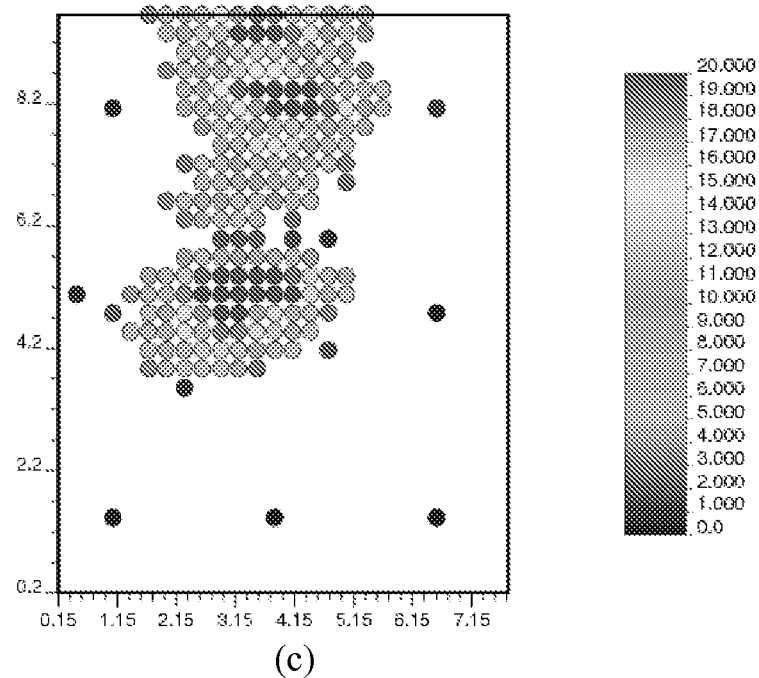
Figure 1:
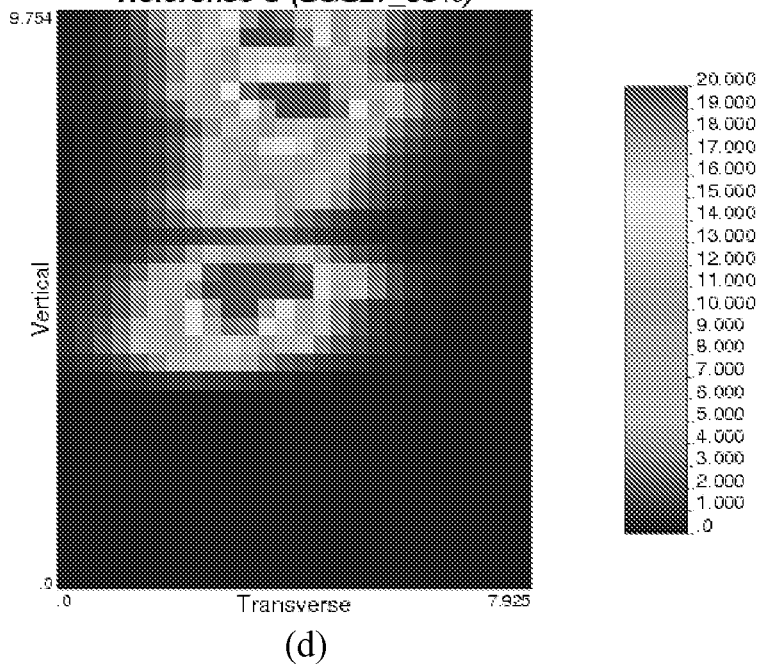

Certain exemplary embodiments of the present invention are described below. The invention is not limited to these embodiments. The spatial sampling design concentrates sampling effort on uncertain locations of the hot spot areas (e.g., areas of high contaminant concentration) in a plane (e.g., contamination plane) thereby significantly improving sampling efficiency. An initial sampling starts the sampling process. In order to maximize the information quality of sample data, the sampling density in the initial stage is kept minimal. For example, nine observations in the initial sampling stage. However, it is contemplated that fewer than nine observations are also possible depending on the situation in the field. It is contemplated that each observation is added one by one, so that the information brought by additional samples is fully used. In this way, every observation represents a sampling stage. For every sampling stage, observations are processed by the geostatistical approach presented herein. The probability distribution of mass discharge and the conditional variance of contaminant concentration (used in one of the sampling criteria) are updated. More observations are obtained and the sampling criteria are updated, as does the amount of information transmitted by each sampling criterion is registered and the weights for sampling criteria are additionally updated with the different sampling stages.

When applied to the sampling in the subsurface, it is contemplated that physical restrictions may only allow several sampling stages, and in each sampling stage, observations may be located along a vertical line (e.g., using Geoprobe down a hole or shaft in the ground).

GeoStatistical Approach

In the geostatistical approach C (contaminant concentration) and K (hydraulic conductivity) are modeled as spatial random variables and the mass discharge is estimated as:

$$M = \sum_{i=1}^{N} -C_i \times K_i \times \text{gradient}$$

Wherein $C_i$ and $K_i$ are the interpolated concentration and hydraulic conductivity values at location i, respectively, N is the number of nodes on the sectionalized control plane. The longitudinal gradient is considered a constant across the control plane because it generally varies little on a plane that is orthogonal to the ground water flow. Application is either at a steady concentration distribution or on concentration measurements taken at particular times (e.g., before and after remediation) to illustrate the evolution of mass discharge.

Cosimulation of K and C Values

It is contemplated that two or more variables can be cosimulated (e.g., simulated jointly) by directly simulating a vectorial random function using sequential simulation algorithms such as Sequential Gaussian Simulation (SGS) (Gómez-Hernández and Journel, 1993; Verly, 1993) or Sequential Indicator Simulation (SIS) (Gómez-Hernández and Srivastava, 1990; Goovaerts, 1997). The difficulty resides in the inference and modeling of the cross-covariance matrix. Not only might there not be enough data for the reliable inference of each covariance function, but all the direct and cross covariance functions must be fit jointly to ensure that the linear model of coregionalization is permissible (Goovaerts, 1997). The implementation becomes even more difficult when Gaussian-related algorithms are not suitable. The indicator-based algorithm requires the joint modeling of a (cross) covariance matrix that not only includes each variable, but all the thresholds for each variable.

It is contemplated that a common method to alleviate the (cross) covariance modeling effort is to define a hierarchy of variables and then simulate each one in turn (Almeida and Journel, 1994), which greatly simplifies the modeling step at the expense of no control on the covariance. Another limitation is the underlying multi-Gaussian assumption (Almeda and Journel, 1004; Grimmet and Stirzaker, 2001) that is unrealistic for the mass discharge problem. Indeed, concentration fields are highly heterogeneous and the multi-Gaussian assumption does not hold even after normal score transformation. The use of a multiGaussian random function model will also cause extreme values to be spatially uncorrelated (e.g., destructuration effect), which is typically not a good assumption for spatial variables such as hydraulic conductivity (Journel and Deutsch, 1993).

The p-Field Simulation Approach

Probability-field simulation was adopted for the algorithm in some embodiments as described herein, which is commonly referred to as 'p-field' simulation, to jointly simulate contaminant concentration and hydraulic conductivity. P-field simulation is a popular algorithm introduced by Srivastava (1992) and further documented by Froidevaux (1993). For example, the effectiveness of this algorithm has been demonstrated in many field applications (e.g. Saito and Goovaerts, 2002; Painter, 2001; Yao and Chopra, 2000; Mao and Journel, 1999; Dungan, 1998). Unlike sequential simulation algorithms, the p-field simulation algorithm separates the task of constructing conditional cumulative distribution functions (ccdfs) from the task of covariance reproduction by using auto-correlated random numbers (p values) to sample the pre-constructed ccdfs. Thus, literally any algorithm can be used to construct ccdfs, and the spatial structure of the target variable is imparted from the spatial structure of the p values. The proposed algorithm uses the indicator-based approach for the construction of ccdfs, and adopts the Markov-type hypothesis to jointly simulate "p-field pairs" for C and K, where the p values are derived from auto-correlated Gaussian random numbers.

Reference Control Planes

To evaluate the performance of sampling designs on the modeling of mass discharge uncertainty, the value of mass discharge is needed. It is contemplated that although true values are not known in the field, numerically simulated control planes can be used in the evaluation and serves the same purpose as field sampled numbers. As such, hypothetical control planes were generated based upon a real field site (Abriola et al., 2005). The generation process was designed to produce physically realistic plume transect data associated with heterogeneous source zones.

Realizations of the permeability field were constructed using the sample data from the Bachman road site, MI (Abriola et al., 2005), where the perchloroethylene (PCE) contaminated aquifer is composed of relatively homogeneous glacial outwash sand. The Kozeny-Carman hydraulic conductivity estimates varied from 1 to 48 m/d, with a log normal variance of 0.29.

Exemplary source zones generated from 2D simulations of the infiltration and entrapment of hypothetical PCE spills were used to select permeability fields that resulted in representative 2D source zones (Lemke et al., 2004). Permeability fields were used to create 3D source zones using a multiphase simulator UTCHEM (Lemke et al., 2004; Christ et al., 2005). The simulation of mass recovery using a modified version of MT3D (Parker and Park, 2004, Water Resourc. Res. 40:W05109) produced the downstream plumes (Christ et al., 2006), and the control planes were selected as the ones that were associated with 98% source mass removal. The spatial patterns of PCE concentration on the control planes are highly heterogeneous, with scattered small hot spots and large near-zero concentration (e.g., PCE contamination is negligible or non-existent) areas that are representative of field situations (FIG. 1d).

Each exemplary reference control plane provides information of concentration field and hydraulic conductivity field. For the example, the size of the control plane was 7.9248 m wide (y) by 9.7536 m high (z). The resolution of the hydraulic conductivity field was 0.3048 m (y) by 0.3048 m (z), based upon the measurement support of the field data. Resolution for the concentration field was 0.3048 m by 0.0762 m (z); while, for this example, a screen length of 0.3048 m (z) was used.

Sampling Criteria

For relatively homogeneous permeability fields, the uncertainty of mass discharge is mainly attributed to the heterogeneity of concentration field. Therefore, the first sampling criterion is for the spatial pattern recognition of the concentration field delineation of the hot spots area. It is contemplated that by applying this criterion, the prediction from geostatistical application is improved. Three different formulations for this sampling criterion were evaluated by the prediction error of mass discharge, where the prediction error was calculated as the difference between the mean of the probability distribution of mass discharge and the true value.

I. Sampling According to the Simulated Value of Concentration

Figure 9:
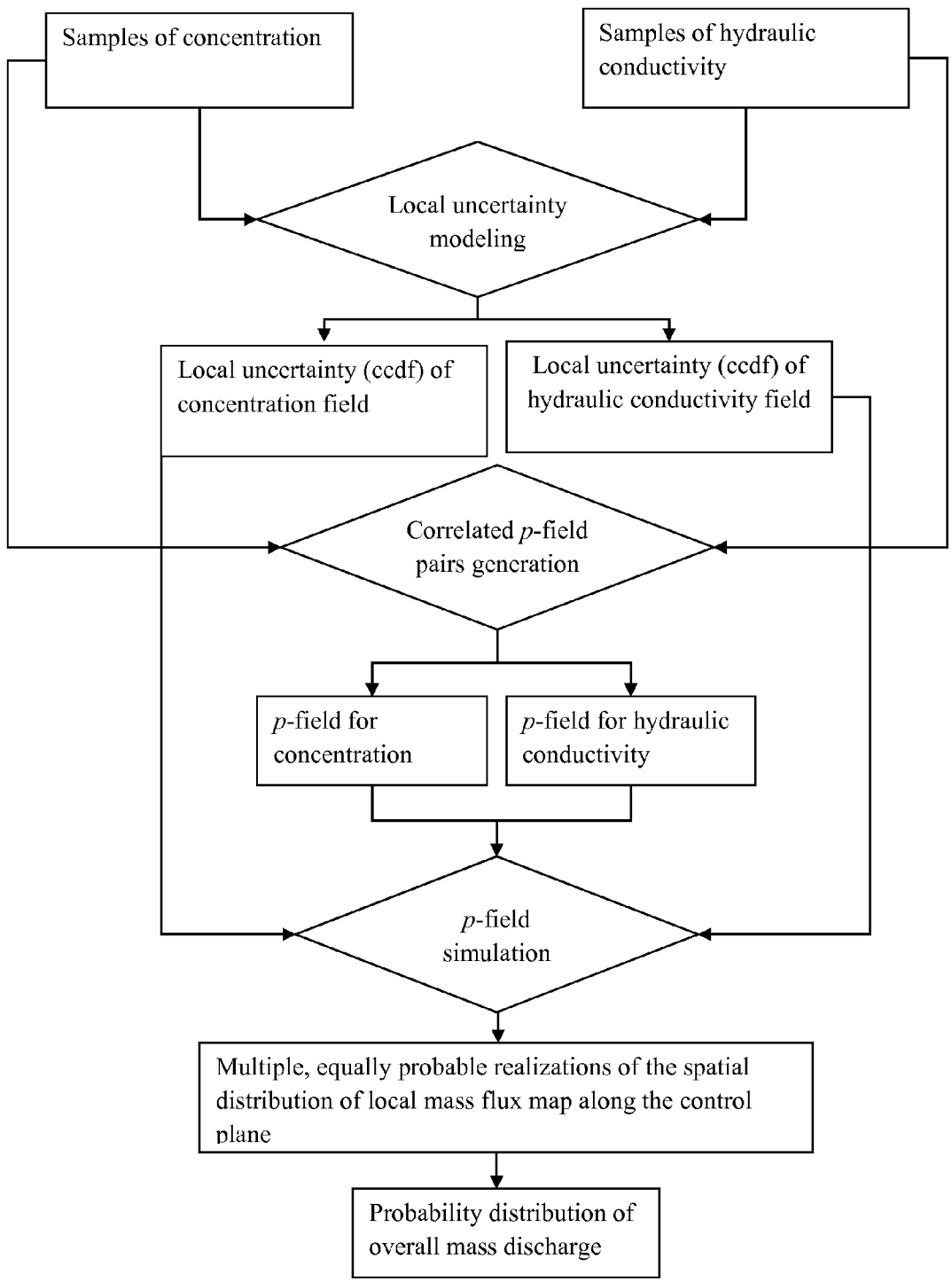
FIG. 9 is a flowchart of the geostatistical approach for uncertainty analysis of mass discharge using multi-level transect data.

For the first formulation, possible sampling locations are ranked according to the simulated values of concentration, and it is contemplated that high concentration values will be located within hot spot areas. Exemplary values were obtained through the geostatistical computer program that models the uncertainty of mass discharge (FIG. 9), where the concentration field was simulated using p-field simulation (Srivastava, 1992, SPE Annual Conference and Exhibition, Washington, D.C., #24753; Froidevaux, 1993, Fourth Intl. Geostatistics Congress, Troia, Portugal). FIG. 1 is exemplary of this formulation by the maps of sampling locations with 25, 65 and 208 observations (e.g., observations added one by one into the simulation). FIG. 1 demonstrates that hot spots were delineated; the delineation started from the center and gradually shifted to the boundary of the field.

II. Sampling According to the Local Entropy of Concentration

Entropy is a measure of information uncertainty (Shannon, 1948, Bell System Technical Journal 7:379-423). The entropy of a random variable (RV) is defined in terms of its probability distribution. For example, Z is a discrete RV that can take K outcome values with probabilities $p_k$, k=1, . . . , K, such that $\Sigma p_k$=1. The entropy (H) attached to this discrete probability set is then defined as:

$$H = -\sum_{k=1}^{K} [\ln p_k] p_k \geq 0$$

Figure 2:
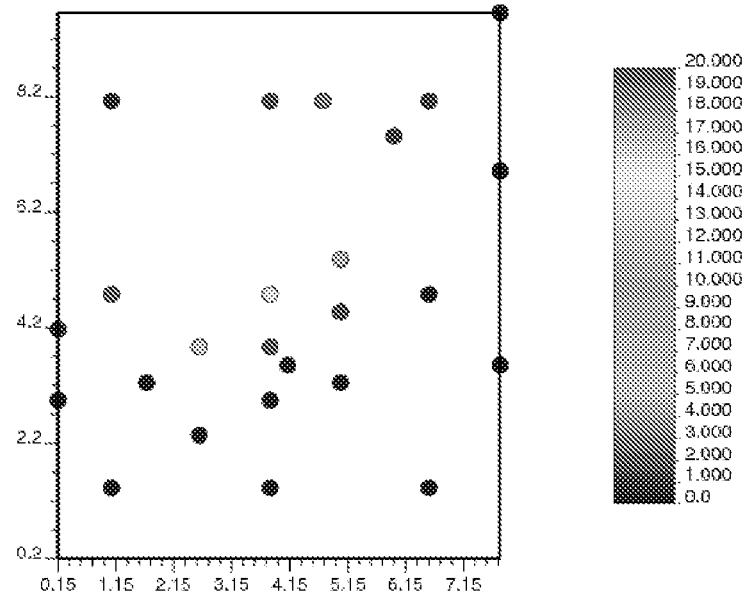
FIG. 2 shows an example of the multi-stage sampling locations according to local entropy (a): 25 observations (b) 45 observations (c) 208 observations (d) reference field.
Figure 2:
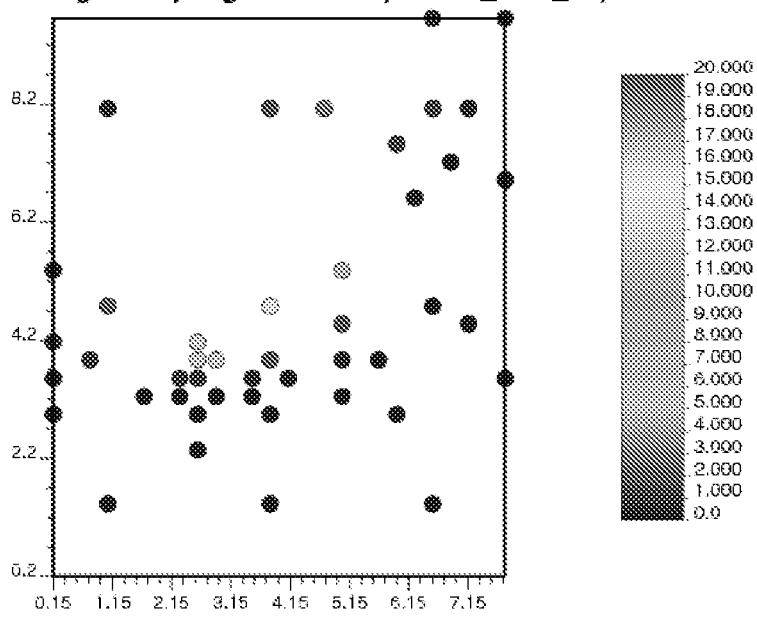
Figure 2:
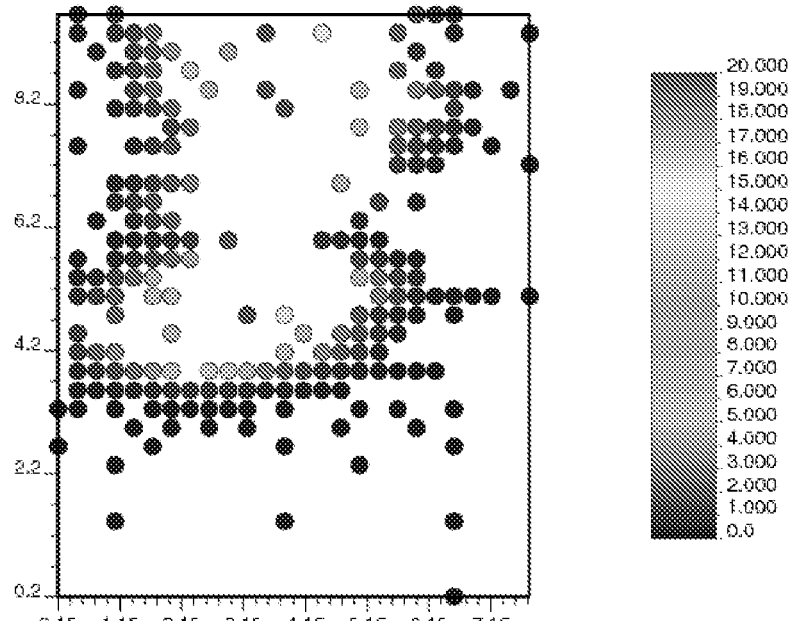
Figure 2:
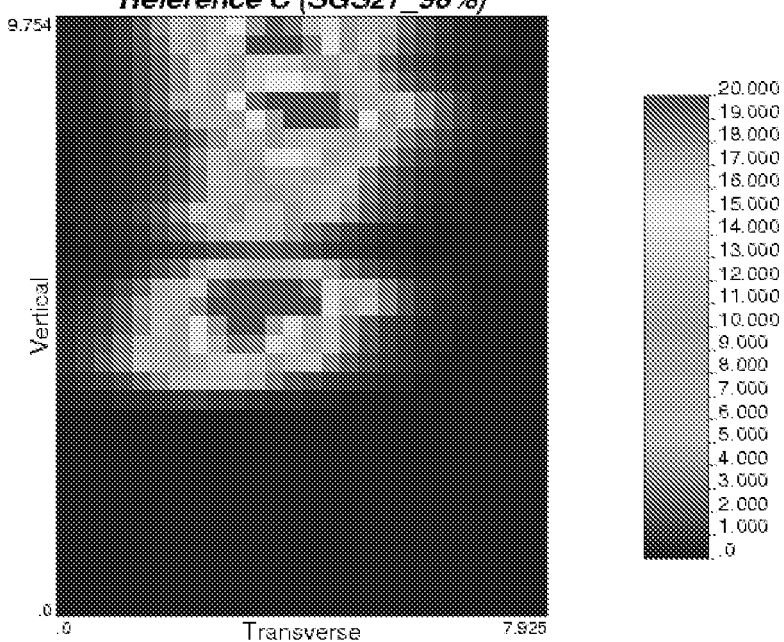

The larger the entropy, the more uncertain is the random variable. Maximum entropy is reached when all outcomes have the same probability of occurrence, and the maximum value is lnK. Local entropy is the entropy of a RV at a specific location, which is a measure of local uncertainty and can be calculated from the local uncertainty model, the conditional cumulative distribution function (ccdf) of the RV. Local entropy of concentration was further tested to locate additional observations. Values of the local entropy were calculated from the ccdfs of concentration, which were modeled by the (ordinary) indicator kriging (Journel, 1983, J. Intl. Assoc. Math. Geol. 15:445-468), a non-parametric method that does not assume any type or shape for the probability distribution of a RV. FIG. 2 shows an example of multi-stage sampling locations using this formulation. The boundary of hot spots are found at very high sampling density (e.g. 25%), however the performance is poor at low sampling density. Moreover, very few observations were actually located in the hot spot area suggesting that the local entropy is not very sensitive to data values.

III. Sampling According to the Conditional Variance of Concentration

Figure 3:
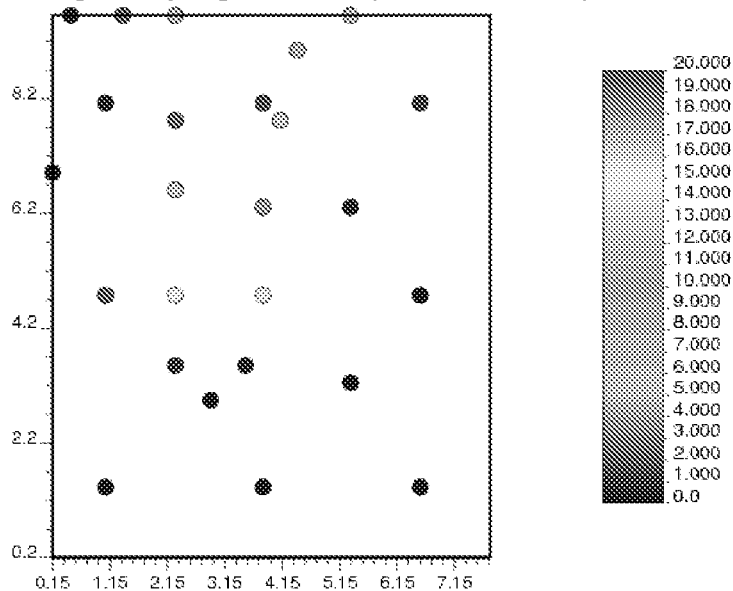
FIG. 3 shows an example of the multi-stage sampling locations according to conditional variance (a): 25 observations (b) 45 observations (c) 208 observations (d) reference field.
Figure 3:
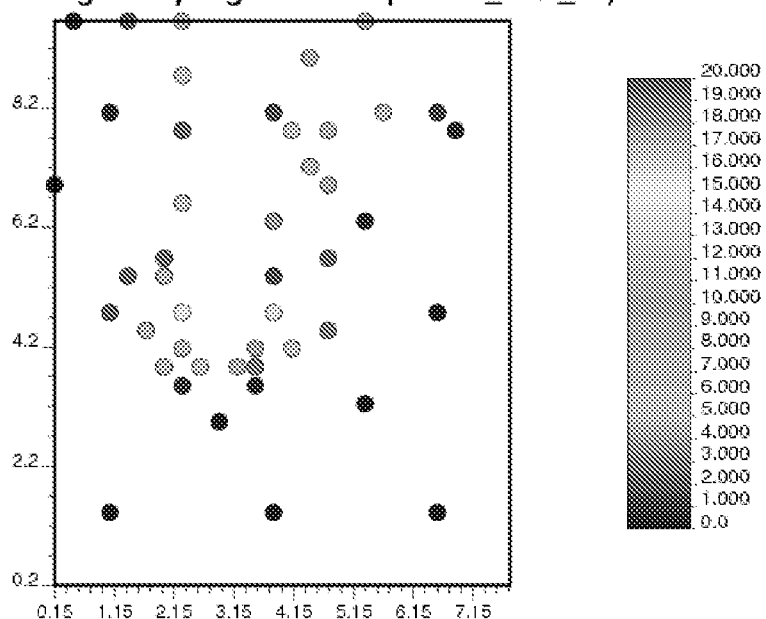
Figure 3:
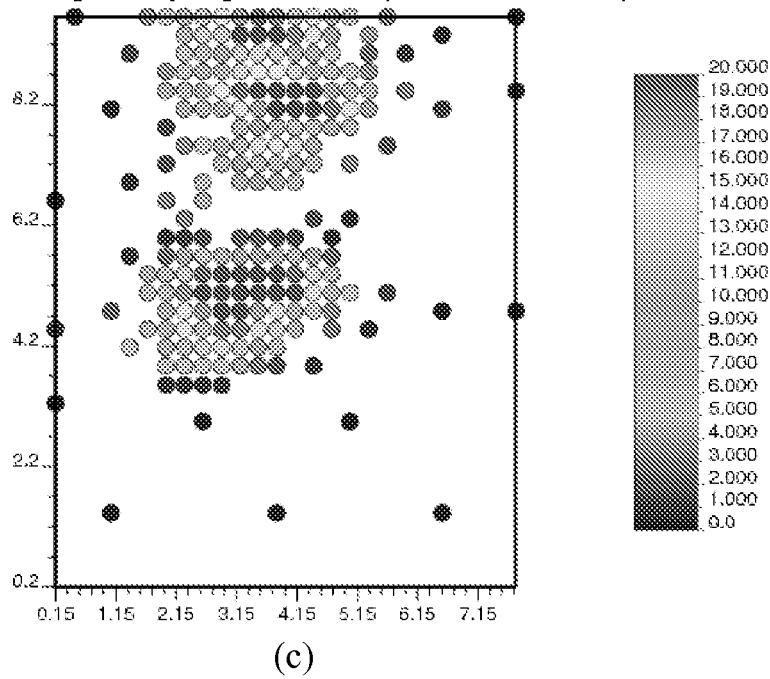
Figure 3:
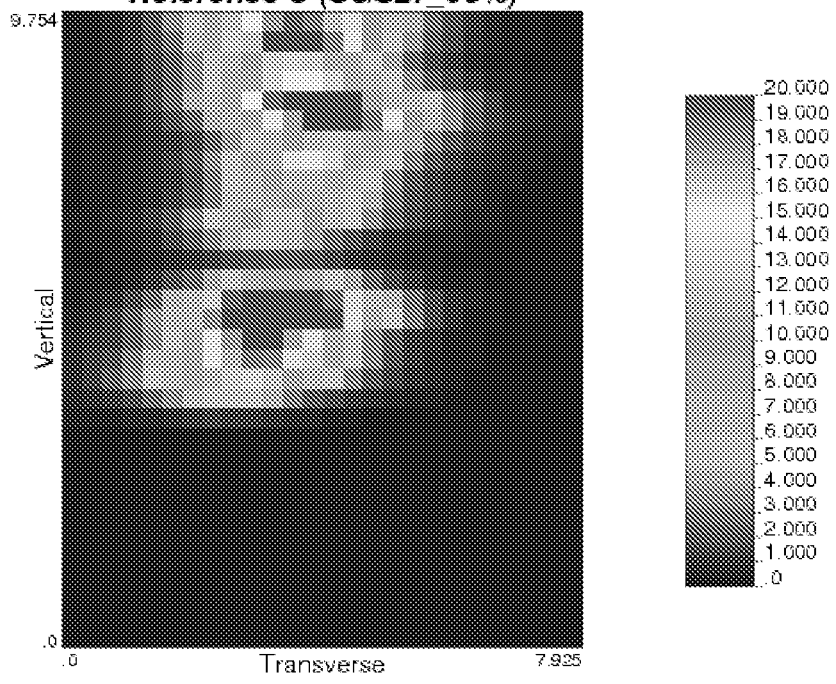

Similar to local entropy, the conditional variance of contaminant concentration is another measure of local uncertainty. Conditional variance is the variance at a specific location. Unlike the entropy measure, the variance is defined around a central value, as such it is contemplated to be more sensitive to data values. As an example, the conditional variance used was calculated from multiple realizations of concentration generated from the p-field simulation, and (ordinary) indicator kriging was used to construct the ccdfs for the p-field simulation. FIG. 3 shows the exemplary sampling locations detected according to the conditional variance. Hot spots were delineated, however opposite to the sampling according to the simulated value, delineation of hot spots was from the boundary to the center.

Figure 4:
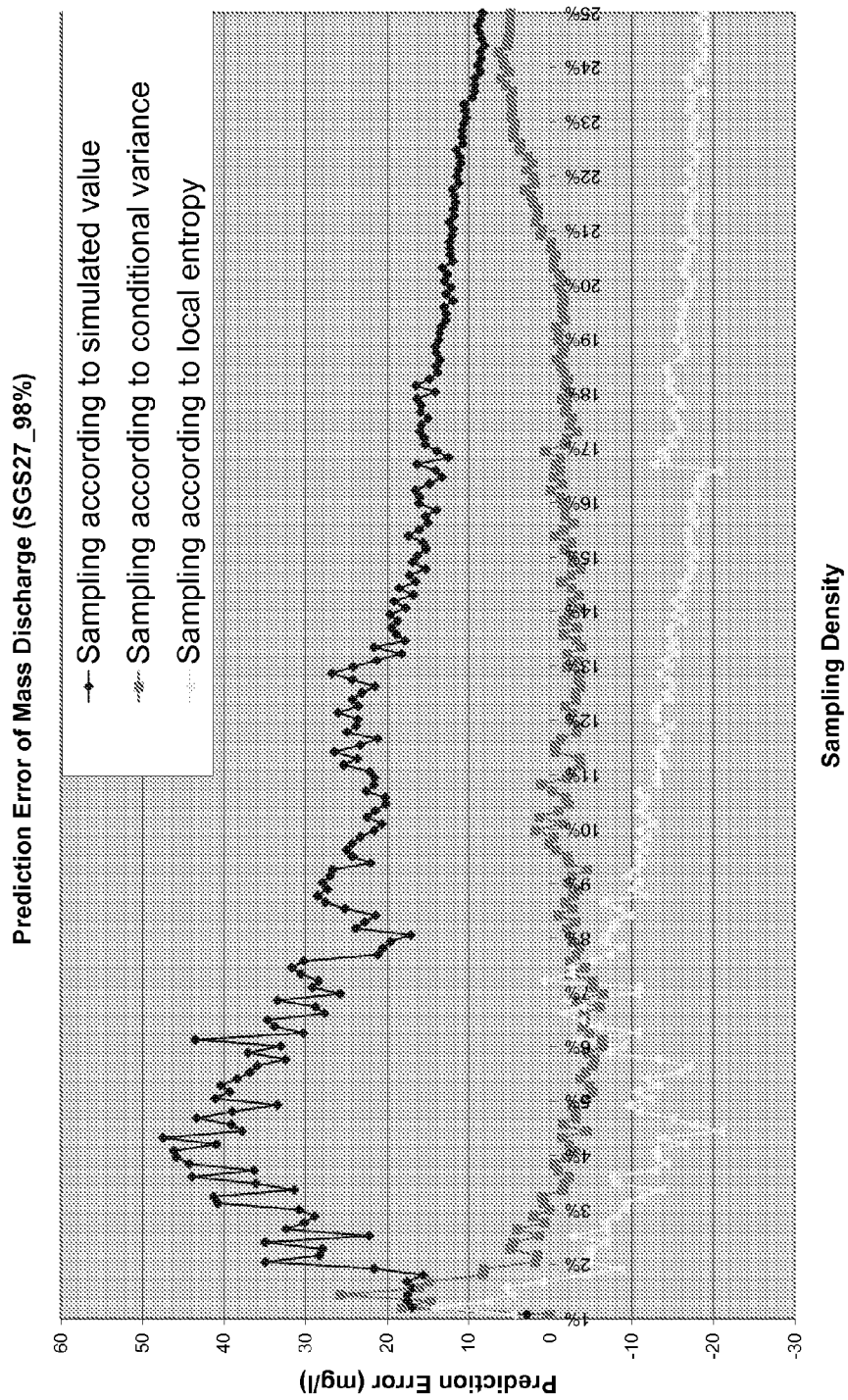
FIG. 4 demonstrates and example of the prediction error of mass discharge using different formulations for hot spot delineation.

The effects of the three different approaches for the delineation of hot spots were assessed by the prediction error of mass discharge, as shown in FIG. 4. FIG. 4 demonstrates that sampling according to the conditional variance of concentration results in the lowest prediction error. Sampling guided by the simulated values results in huge positive error in early sampling stages. The positive error is due to the delineation of hot spots starting from the center where there is very limited information in between the hot spot area and the near-zero concentration area. Therefore, uncertainty in predicting the boundary of a hot spot area is very high due to sparse sampling. When sampling according to local entropy, most observations were located outside of a hot spot area thus, the mass discharge was severally underestimated. Underestimation occurred because local uncertainty measurements are not sensitive to data values, unlike conditional variance. Conditional variance is a measure that considers both the local uncertainty and the data values. At locations that are adjacent to "hot" observations, conditional variance is low because there is less local uncertainty due to existing observations. However, locations that are close to near-zero observations are also low in conditional variance because data values are low. As a result, the sampling priority is the boundary of a hot spot area. In one embodiment, the present invention provides a first sampling criterion formulated as the conditional variance of concentration. In some embodiments, said conditional variance is calculated from multiple realizations of concentration generated from the p-field simulation, wherein indicator kriging is used to construct the ccdfs for the p-field simulation.

IV. Second Sampling Criterion

The second sampling criterion is adapted from the MMSD criterion proposed by van Groenigen and Stein (1998). The criterion ensures coverage of the entire domain, so main features of the spatial distribution are captured. For each possible sampling location, the distance between the location and its nearest observation is calculated as:

$$L_i(x_i, S)\ i=1,\ldots,m$$

where $L_i(x_i, S)$ is the Euclidian distance between any location,
$x_i$ and the nearest sample, and
m is the total number of possible sampling locations.

When sampling according to the rank of $L_i$, additional sample points are located in the region with sparest observations. This criterion is an important component; the identification of hot spots using conditional variance requires that at least one observation be within the neighborhood of hot spot area (although not necessarily at the center). For example, under the circumstance that all of the observations in the previous sampling stage(s) hit non-hot spot area this criterion dominants the sampling design. The extreme case is that all of the concentration observations are zero. In an exemplary situation where all observations are zero, the conditional variances at all locations are also zero, which provides no information for the next sampling location. If this outcome is reached, then it is contemplated that the next sampling location is the one with the least number of observations in its neighborhood. In one embodiment, the present invention provides a second sampling criteria adapted from the MMSD criteria, such that the main features of the spatial distribution are captured.

Compromise Solution and Weights Assessment

The methodology in Multiple Criteria Decision Making (MCDM) was adapted for (1) scaling of sampling criteria, (2) locating the next observation, and (3) managing the weights for each criterion. It is contemplated that by adapting the methodology in MCDM, essentially every possible sampling location is viewed as an alternative in decision making, and sampling criteria are viewed as the attributes.

Scaling of Sampling Criteria

The sampling criteria can be scaled to the interval [0, 1] using the fuzzy membership function that measures the closeness of the value of the ith criterion to its ideal value. The possible values of the ith criterion are viewed as a fuzzy set, defined as (Zeleny, 1982)

$$\{x_i^k, d_i^k\}\ i=1,\ldots,n\ k=1,\ldots,m$$

Where $d_i^k$ is a membership function scaling the value into the interval [0, 1] using the ideal value of $x_i^k$,
Wherein m is the total number of possible sampling locations,
Wherein n is the number of criteria.

The "ideal" is different from the definition in MCDM, but in both cases, "alternatives that are closer to the ideal are preferred to those that are farther way". For example, for the sampling criterion of conditional variance, the location with a higher conditional variance is preferred. There are different methods to calculate $d_i^k$ using $x_i^k$ and $x_i^*$, depending upon the situation of the ideal [Zeleny, 1982]. It is contemplated that the ideal is a maximum, since it is preferable to situate the next observation at the location with the highest conditional variance and the longest distance to the nearest sample. The function for the calculation of $d_i^k$ is then [Zeleny, 1982]:

$$d_i^k = \frac{x_i^k}{x_i^*}$$

Locating the Next Observation

The next sampling location is decided by the compromise solution with the composite membership function that is used when multiple criteria present. The composite membership function is defined as (Zeleny, 1982):

$$L_p(\lambda, k) = \left[\sum_{i=1}^{n} \lambda_i^p (1 - d_i^k)^p\right]^{1/p}$$

Where $L_p$ is the composite membership function for the kth alternative (sampling location), and $\lambda_i$ is the weight for the ith attribute (sampling criterion). The compromise solution is obtained by the minimization of $L_p$ with respect to p. P represents the distance parameter that takes any value in $[1, \infty]$. As p varies from 1 to infinity, the emphasis on the largest individual deviation among n attributes is shifted from the weakest to the strongest. When p=1 the minimization of $L_p$ reflects the extreme disregard of individual deviation and the emphasis is on the total sum of n deviations. For p=∞, minimizing $L_p$ means minimizing only the largest deviation among n attributes. Besides $\lambda$, p represents another way to weight across attributes (e.g., weighting considering the deviation magnitudes across attributes). For example, if p=∞, given the information brought by sampling criteria is important (expressed in $\lambda$), if one sampling criterion indicates great interest of sampling at current location, then this location is sampled. As an example, p=1 was used and the weighting was only decided by the information importance of sampling criteria.

Managing the Weights for Each Criterion

The weight $\lambda_i$ is decided by the importance of the information transmitted through the ith sampling criterion. The magnitude of the "importance" is decided by the "contrast intensity" of the values of the ith attribute among m possible alternatives. For example, consider that the values of the conditional variance at all of the possible sampling locations are the same. This sampling criterion does not provide any "decision information". Thus, the more distinct and differentiated are the conditional variance values (e.g., the larger the contrast intensity), the greater is the amount of decision information; hence the more important is this criterion. The magnitude of the importance can be measured by information entropy. The entropy measure of the contrast intensity of the ith criterion is defined as (Zeleny, 1982):

$$e(d_i) = -K \sum_{k=1}^{m} \frac{d_i^k}{D_i} \ln \frac{d_i^k}{D} \geq 0, \quad K > 0$$

$$D_i = \sum_{k=1}^{m} d_i^k \quad i = 1, \ldots, n$$

When there is no contrast among the m values of the ith criterion (e.g., all of the $d_i^k/D_i$ equals 1/m, $e(d_i)$ reaches its maximum value K ln m. Thus, by setting K=1/ln m $e(d_i)$ is normalized to the interval [0, 1].

The weight $\tilde{\lambda}_i$ is reversely related to $e(d_i)$ (Zeleny, 1982):

$$\tilde{\lambda}_i = \frac{1}{n-E}[1 - e(d_i)] \left( \sum_{i=1}^{n} \tilde{\lambda}_i = 1, \quad 0 \leq \tilde{\lambda}_i \leq 1 \right)$$

$$E = \sum_{i=1}^{n} e(d_i)$$

Decision maker's opinions for weights are introduced at this point, and the combination of $\tilde{\lambda}_i$ and the decision maker's judgment can form a final weight $\lambda_i$. $\tilde{\lambda}_i$ was is used as the exemplary final weight.

Following the derivation, the composite membership function becomes:

$$L_i(\lambda, k) = (\lambda_1 d_1^k + \lambda_2 d_2^k)$$

-continued

With $$\lambda_i = \frac{1}{n-E}[1 - e(d_i)] \quad (\lambda_1 + \lambda_2 = 1, \quad \lambda_1 \in [0, 1])$$

$$d_i^k = \frac{x_i^k}{x_i^*}, \quad i = 1, 2$$

The compromise solution is obtained by minimizing $L_1(\lambda, k)$ (e.g., maximizing $\lambda_1 d_1^k + \lambda_2 d_2^k$. It is contemplated that $\lambda_1$ and $\lambda_2$ are updated at each sampling stage since $x_i^k$ receive new values at each sampling stage; and the "displaced ideal", the maximum value among all $x_i^k$ is updated.

The method as presented herein is for the situation that additional observations are added one by one on a control plane. Hence, the coordinates of the next sampling location could be different from the previous location in both vertical and horizontal directions. For the implementations in the subsurface, however, it is most likely that sampling should follow vertical lines (e.g., drilling holes). Thus, the restricted sampling design considers each vertical line as a sampling stage, and identifies the location of the next vertical line according to the line average of the composite membership functions. In this way, the control plane is sampled in consecutive vertical lines. For each line, the vertical coordinates of the depths are decided at one time by sorting the composite membership functions along the identified line, or the depths are added one by one, where the identification of the next depth benefits from the information brought by the previous depth.

Accuracy Plot

Figure 6:
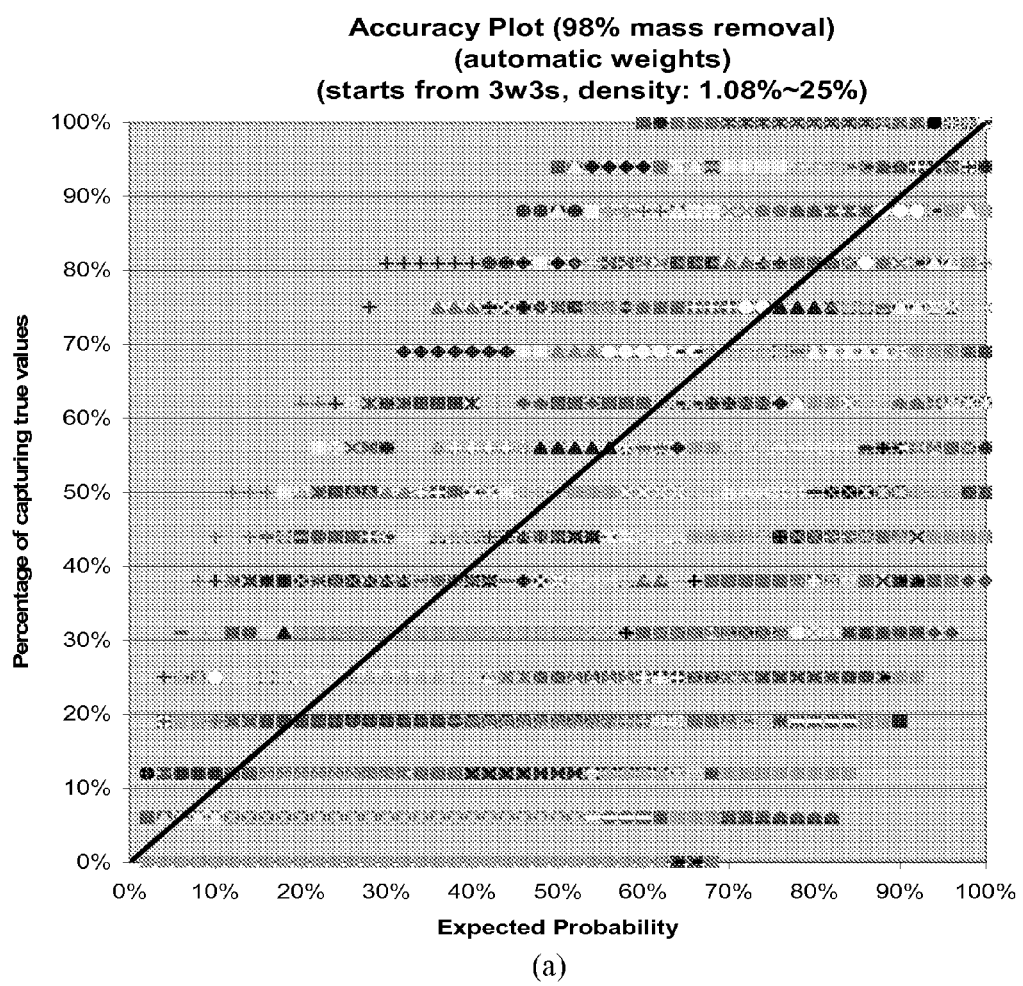
Figure 6:
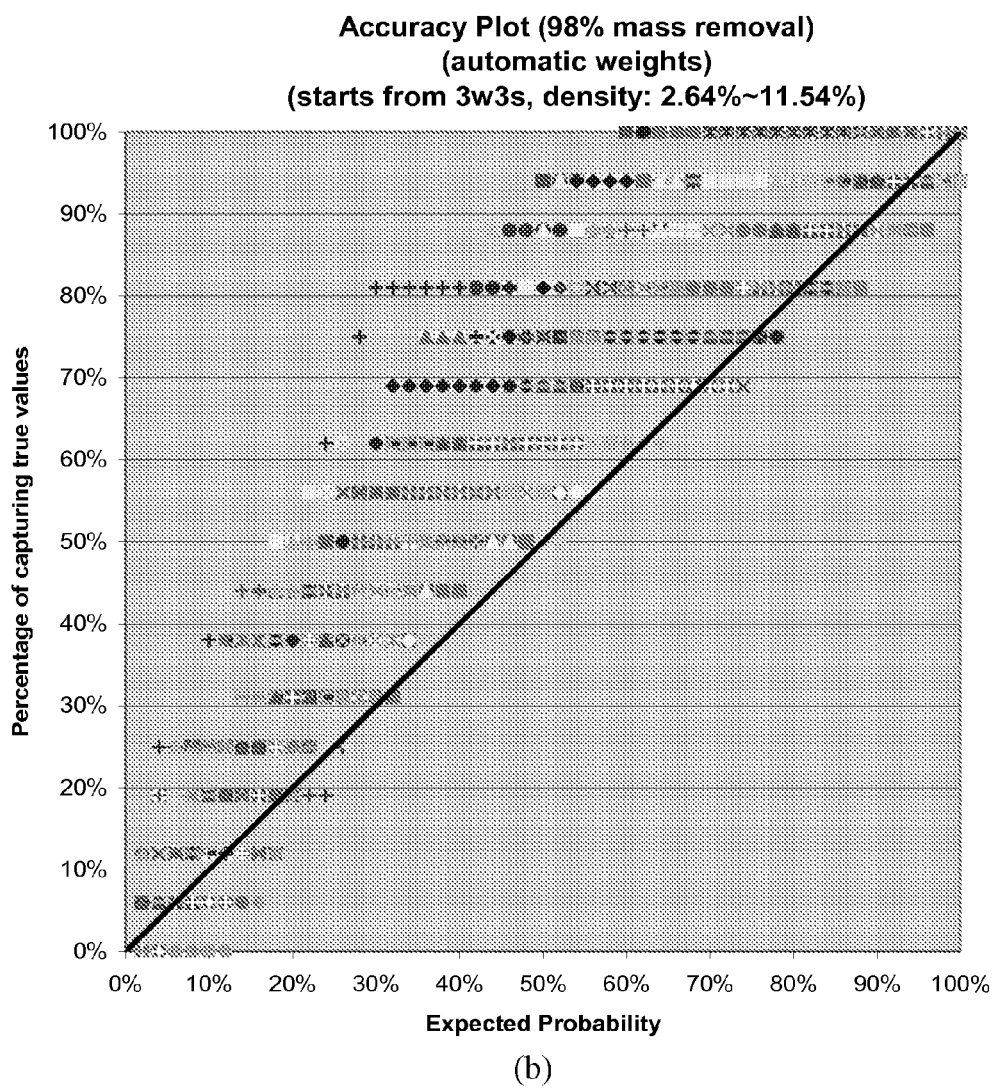
Figure 6:
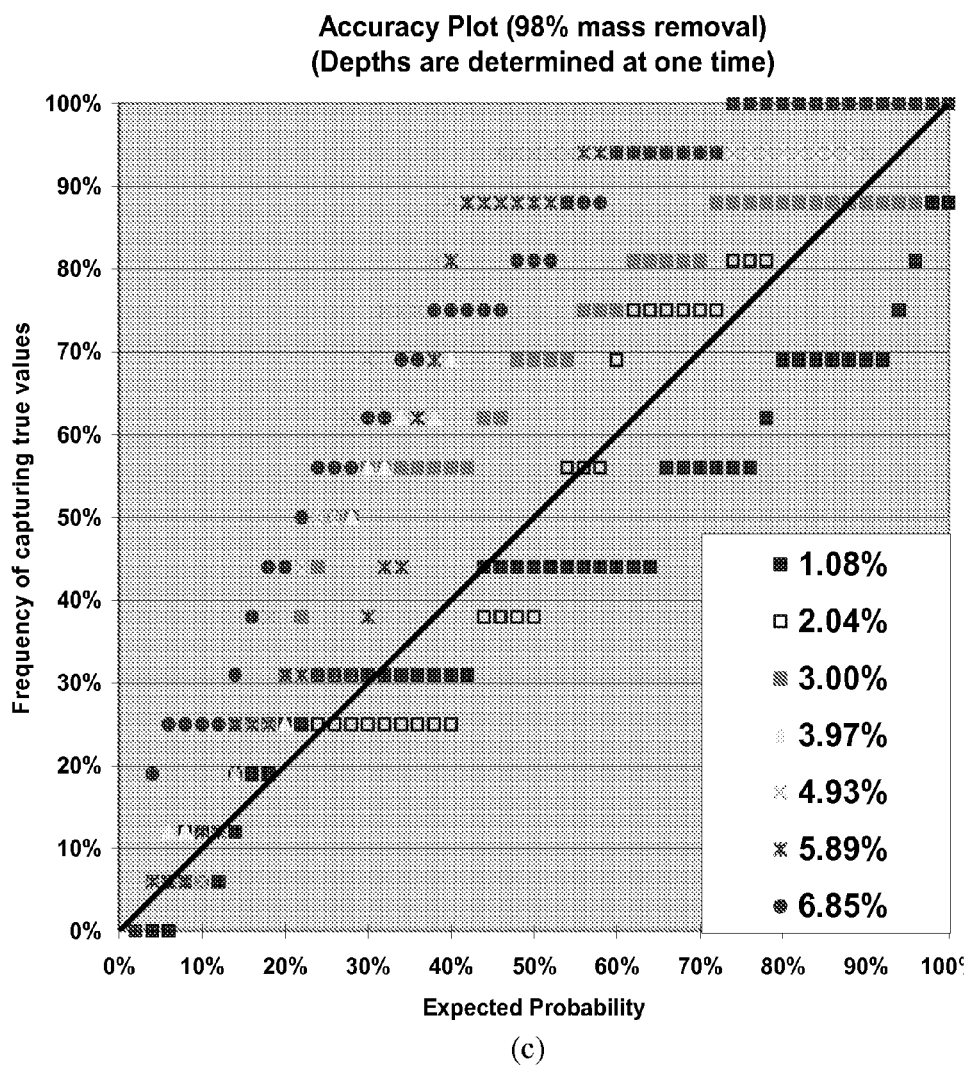
Figure 6:
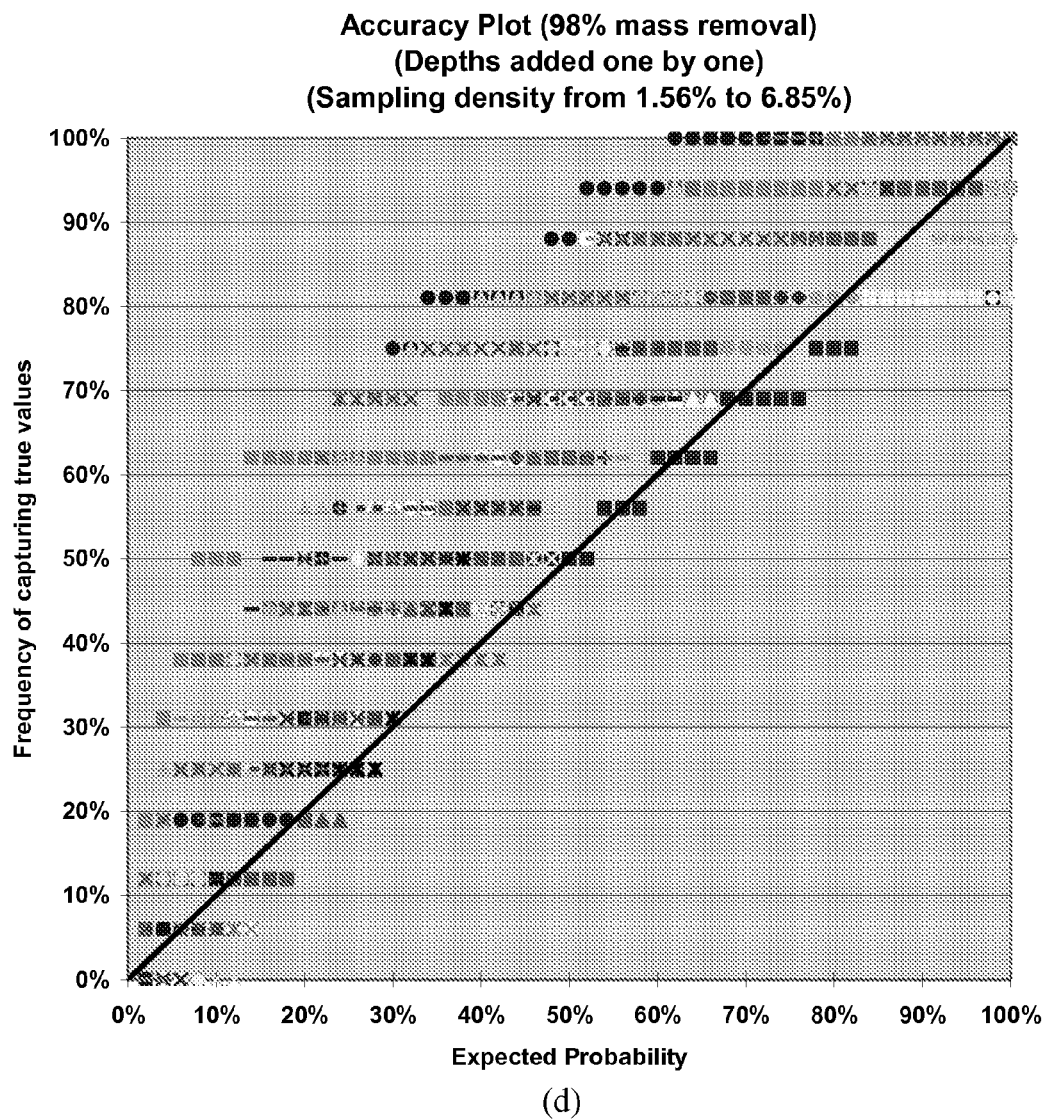

It is contemplated that the optimal sampling density is decided according to the accuracy assessment of the uncertainty model of mass discharge. The assessment is performed by the tool called "accuracy plot". FIG. 6a shows an example of grouped accuracy plots, wherein different symbols represent different sampling densities. Originally proposed by Deutsch (Deutsch, 1997, Quant. Geo. Geostat. 8:115-125), the accuracy plot herein adapted is used to count the occurrence of capturing true values among 16 reference fields. An accuracy plot depicts frequency of occurrence of the true values within a series of symmetric p-probability intervals (PI) bounded by the (1−p)/2 and (1+p)/2 quantiles, where the p-PIs are computed from the probability distribution of mass discharge that corresponds to a specific sampling design for each reference field. For example, to create one accuracy plot in FIG. 6a, a certain sampling design is first decided. In FIG. 6, the multi-stage sampling design with 50 observations (a sampling density of 6%) is used. By sampling the 16 reference fields and processing the 16 sets of sample data (50 for each set), 16 probability distributions of mass discharge can be obtained. A series of symmetric p-PIs with p varying from 2% to 100% (50 p-PIs in total) are calculated from the 16 output probability distribution, and for each p-PI the frequency of capturing the true values (calculated from the 16 reference fields) is calculated. The plot of the frequency in a function of p-PI is the accuracy plot for the sampling density of 6%. An uncertainty model is accurate if the frequency of true values falling in the p-PI exceeds p for all p-PIs (Deutsch, 1997), which, shown on the accuracy plot, is all of the points falling above the 45° line.

Figure 5:
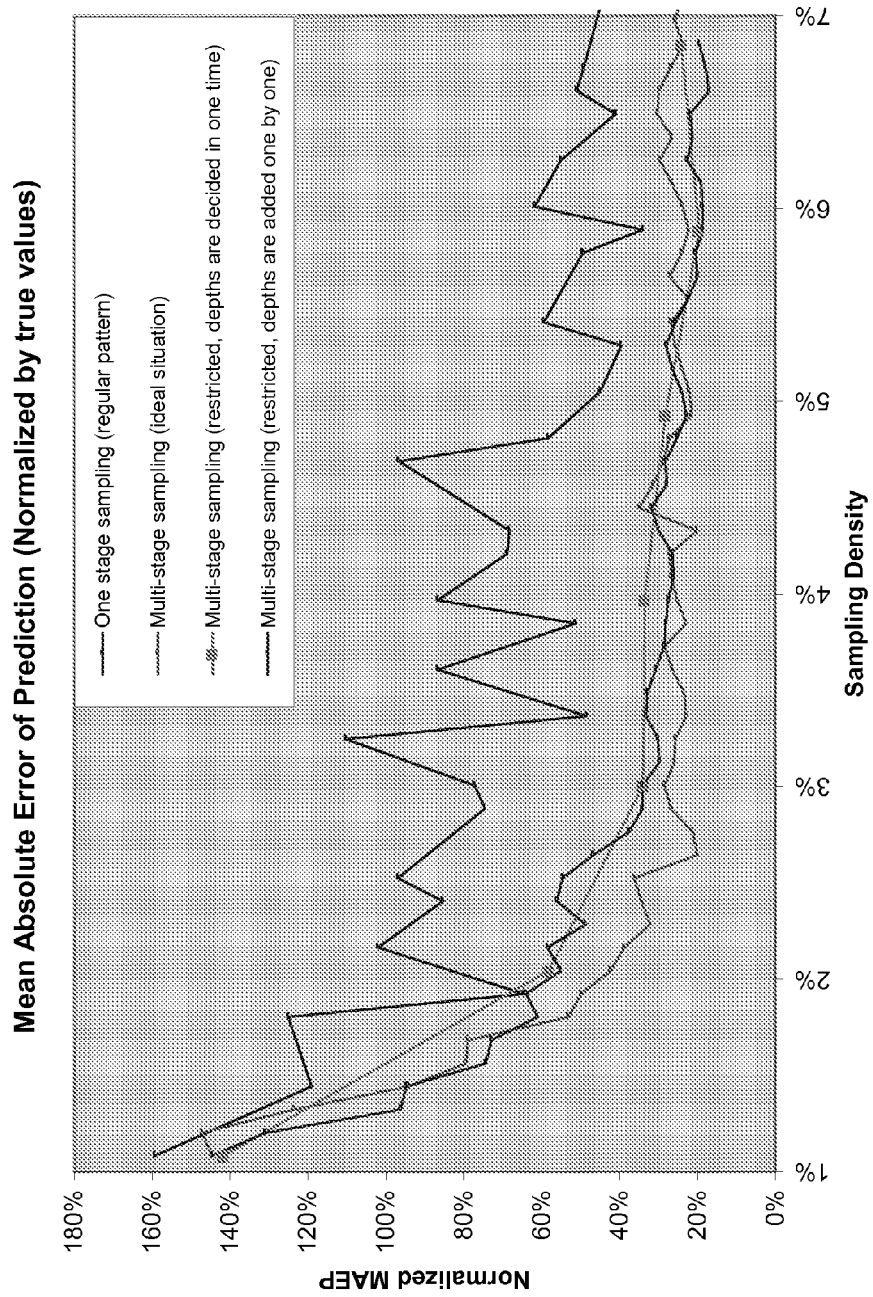
FIG. 5 shows exemplary normalized Mean Absolute Error of Prediction for the ideal and restricted multi-stage sampling designs FIG. 6 demonstrated examples of grouped Accuracy plot of multi-stage sampling. Different symbols represent different sampling densities; (a) Grouped accuracy plot for the ideal situation (sampling density: 1%-25%), (b) Grouped accuracy plot for the ideal situation (sampling density: 2.64%-10.54%), (c) Grouped accuracy plot for the restricted situation (depths added in one time), (d) Grouped accuracy plot for the restricted situation (depths added one by one).

In one embodiment, the multi-stage sampling design as described herein aims to optimize the sampling locations, so that the spatial pattern can be recognized with fewer observations, sample data are more representative, and the geostatistical prediction is thus more accurate. The benefit on geostatistical prediction is illustrated in terms of the Mean Absolute Error of Prediction (MAEP), which is defined as the average of the absolute prediction errors of mass discharge over the 16 reference fields (FIG. 5). FIG. 5 suggests that the multi-stage sampling designs caused much lower MAEP at all sampling densities. Starting from a sampling density of 2%, the MAEP was reduced by 20~40% of the true value of mass discharge in comparison with one stage design.

This benefit is especially significant at low sampling densities. The restricted design causes slightly larger MAEP than the ideal situation, but is still smaller than the MAEP of one stage sampling design. The restricted design was carried out in the way that 6 lines were added consecutively, and for each line, 8 depths were added. User of the coded sampling design tool is able to decide whether or not to add an additional line, and how many depths should be on this line. Whether the coordinates of the depths on each line are decided one by one or decided at one time did not significantly affect the MAEP. It is contemplated that this occurred because in this example, eight depths were designed for each line, which brought a relatively high resolution vertically.

According to the accuracy plot for one stage sampling design with a regular (rectangular) sampling pattern, a sampling density no less than 6~7% is needed for an accurate model of mass discharge uncertainty for the type of concentration distributions shown in the reference fields. For example, using the same reference fields, the accuracy plots for the multi-stage sampling design are shown in FIG. 6. FIGS. 6*a* and 6*b* demonstrate that for the ideal situation, when sampling density is higher than 2.54%, the uncertainty model is accurate (all of the points are above 45° line). For the restricted situation, a sampling density of about 2% is contemplated (FIG. 6*c*, 6*d*). Thus, the detected minimal sampling density for an accurate modeling of uncertainty is 2~3%. This minimal sampling density is reduced by at least 50% in comparison with the one stage sampling design. The improvement of the accuracy of the uncertainty model is resulted from the improved accuracy and precision of the probability distribution of mass discharge.

Figure 7:
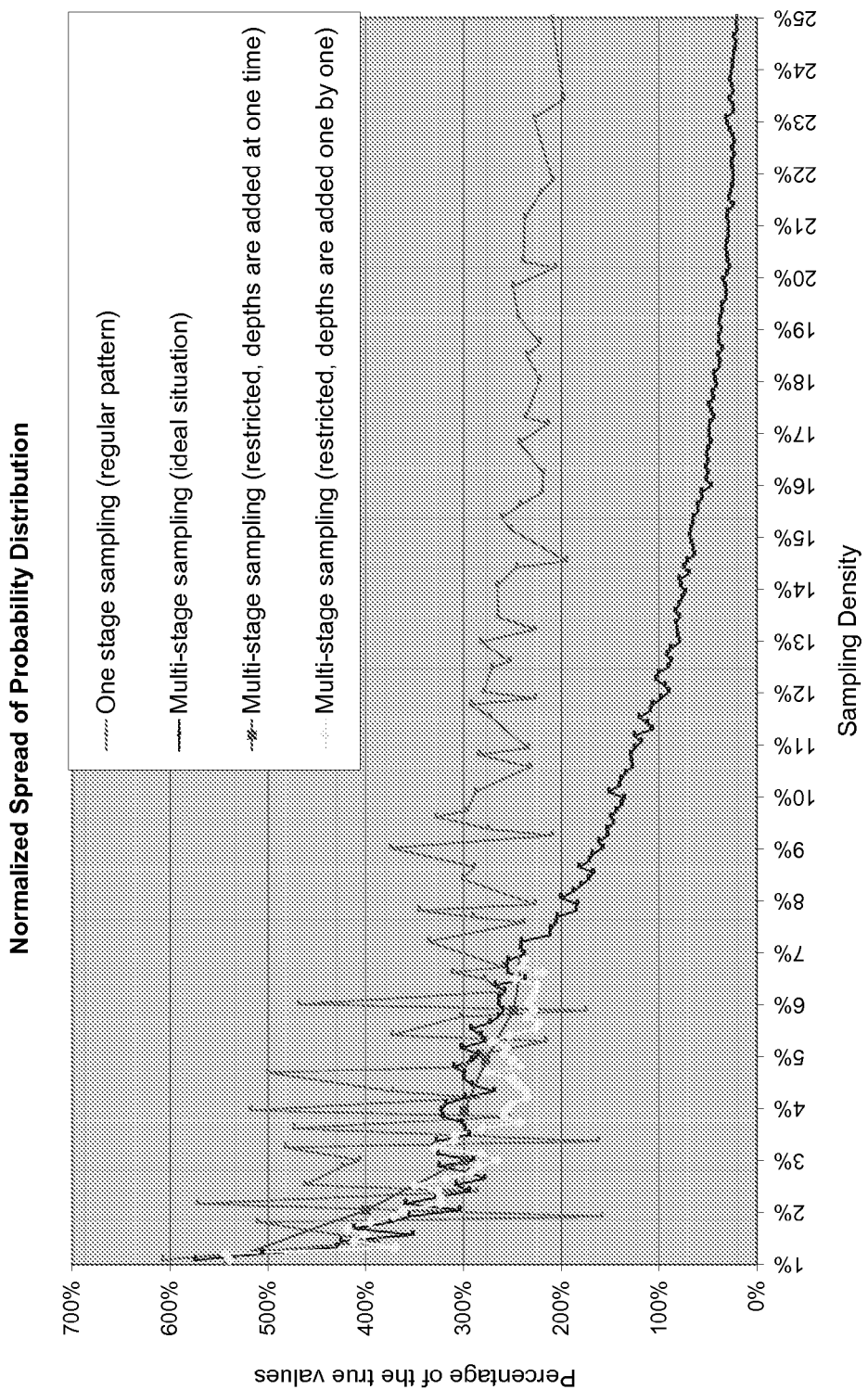
FIG. 7 demonstrated an example of the average spread of the probability distribution of mass discharge, normalized by true values.

FIG. 7 shows the precision measure, the spread of the probability distribution. In FIG. 7, the average spread of the probability distribution is generally narrower for the multi-stage sampling design, and the improvement of precision is significant with the increase of sampling density, due to the delineation of hot spots. Note that when sampling density is very high (e.g., larger than 10%, test of the multi-stage sampling design on the 16 reference fields suggested) there was risk that the uncertainty model was no longer accurate, according to the accuracy plot. At this point, almost all of the hot spot areas were fully sampled (e.g. FIG. 3*c*), thus the realizations of mass flux ($[M/T \cdot L^2]$) become quite similar (mass discharge prediction is obtained by aggregating the values of mass flux); therefore the spread of the probability distribution becomes very small (FIG. 7).

In one embodiment, the present invention provides a multi-stage sampling design for the uncertainty modeling of contaminant mass discharge. The method as described herein is different from previous research works in that the MCDM theory is used to find the optimal sampling locations. Use of the MCDM method is for the adoption of an adaptive sampling type sampling criterion, the conditional variance of concentration, which can only be computed after real sampling occurs. In some embodiments, as a sampling criterion, the conditional variance is effective in the identification and delineation of hot spots. The implementation of the MCDM theory also allows an objective way to weighting multiple sampling criteria, where the weights can be decided by the entropy measured information importance of each criterion. An advantage of this method is that the weights can be updated automatically as the sampling progresses. It is contemplated that the method is not limited in the quantification of mass discharge uncertainty, but can be applied to many other spatial surveys.

Is some embodiments, the present invention can be used to delineate highly concentrated areas which contribute to mass discharge, or highly concentrated areas of other materials. For example, the present invention can be applied to highway construction to find hot spots of weak materials such that special treatments in those areas can be applied. Further, in the mining industry the present invention can be used to find deposits of ore, or "hot spots" of ore, and the like. For soil contamination, the present invention finds utility in locating polluted areas for remediation. For wildlife and fisheries, fish and wildlife density can be determined using the methods of the present invention. Thus, the systems and methods of the present invention find use in a variety of settings.

For mass discharge, the improvements of spatial pattern recognition and the representative condition of sample data, the results for geostatistical applications are equally improved. For example, the prediction errors of mass discharge are generally reduced by about 20~40% in comparison with one stage sampling design at the same sampling density. The improvement of the accuracy and precision of the probability distribution of mass discharge results in a better uncertainty model, compared to a one stage sampling design at the same sampling density. As a result, the required sampling density is reduced by more than 50% for an accurate model of uncertainty.

Figure 8:
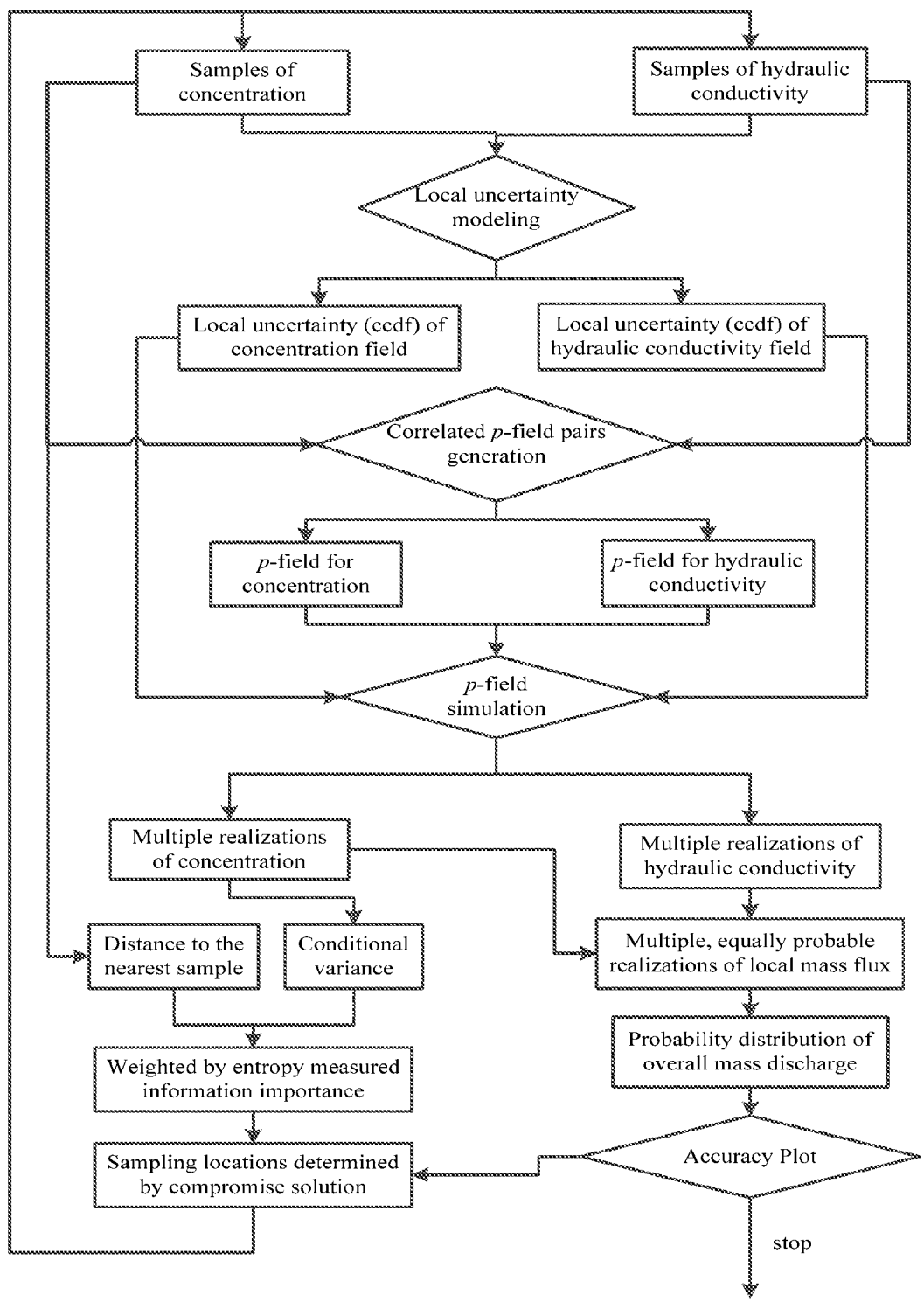
FIG. 8 is a flowchart for defining multi stage sampling locations based on the performing the method of the present invention.

In one embodiment, the multi-stage sampling design has programmable utility as a real-time sampling tool. For example, a computer program is contemplated that incorporates the method as described herein. In some embodiments, the present invention provides a computer program to perform one or more of the functions as seen in FIG. 8. For example, for real-time field measurements, the computer code is capable of identifying the location for the next sampling line (e.g., drilling hole) as well as the sampling locations on this line. It is contemplated that the implementation of this sampling tool will save tremendous sampling cost in terms of time and required number of observations. The systems and methods may be provided via a small handheld electronic device (e.g., PDA, computer, phone, etc.), via a traditional computer system (e.g., laptop, desktop, etc.), via a communication network (e.g., interne service), or any other computing means now known or later developed.

In one embodiment, the present invention provides a method that finds utility in the environmental and geotechnical industries. As such, the present invention provides systems comprising components of such industries in conjunction with components that provide solutions according to the present invention. For example, the method as defined herein could be used in conjunction with Geoprobe® rigs for defining hotspots of oil deposits for drilling. As well, the method finds utility in ground contamination remediation, such that it defines sampling locations for sampling by, for example, Enviro-Care® sampling systems or Waterloo Groundwater Profiler systems. It is contemplated that the present invention finds utility in conjunction with any drilling and sampling system as a way to designate sampling location and frequency. In some embodiments, the present invention provides methods for use in atmospheric sampling and soil physics. In some embodiments, the present invention is used in conjunction with Geographic Information System (GIS) software and technology. In some embodiments, the present method finds use in EVS (Environmental Visualization Systems) graphics. In some embodiments, the interface with the algorithm is via a statistical computer program, such as Excel®, SigmaStat®, Prism® Graphics, and the like.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for selecting optimal sampling locations for mass discharge analysis comprising:
    a) obtaining measurements of contaminant concentration and hydraulic conductivity from a plurality of samples comprising a contaminant from set of initial sampling locations,
    b) using a computer to perform the steps of: i) generating a probability distribution of mass discharge using said measurements,
    ii) estimating conditional variance of contaminant concentration and local sampling density from said measurements at each of said sampling locations,
    iii) using said conditional variance as the first sampling criterion, and local sampling density as the second sampling criterion, calculating membership functions of said sampling criteria at each of said sampling locations;
    iv) calculating information entropy for said conditional variance and said local sampling density;
    v) automatically calculating weights using said information entropy for said conditional variance and said local sampling density; and
    vi) selecting one or a plurality of different sampling locations for a next sampling location from said sampling locations by ranking said candidate locations using the numeric value of a compromise solution at each of said candidate locations;
    c) obtaining additional contaminant concentration and hydraulic conductivity measurements from said selected sampling next sampling locations; and
    d) using a computer to perform the steps of i) updating said probability distribution of mass discharge using said additional measurements; and
    ii) generating an accuracy plot of said probability distribution of mass discharge.

2. The method of claim 1, wherein said information entropy is calculated as follows:

$$e(d_i) = -K \sum_{k=1}^{m} \frac{d_i^k}{D_i} \ln \frac{d_i^k}{D_i} \geq 0, K > 0 \; D_i = \sum_{k=1}^{m} d_i^k \; i = 1, 2$$

where $e(d_i)$ is the information entropy for said conditional variance or said local sampling density, K is the maximum entropy value and equals $1/\ln m$.

3. The method of claim 2, wherein said weights are calculated as follows:

$$\lambda_i = \frac{1}{n - E}[1 - e(d_i)] \; (\lambda_1 + \lambda_2 = 1, \lambda_1 \in [0, 1])$$

where $\lambda_1$ and $\lambda_2$ are said weights for said conditional variance and said local sampling density respectively, and $$E = \sum_{i=1}^{n} e(d_i).$$

4. The method of claim 1, further comprising repeating steps b) through d).

5. The method of claim 1, wherein said generating a probability distribution of a mass discharge within a control plane is performed by:
    a) providing a processor configured to obtain measurements of contaminant concentration and hydraulic conductivity from a sampling,
    b) utilizing said processor to model conditional probability distributions of contaminant concentration and hydraulic conductivity using said measurments,
    c) creating realizations of spatial distributions of contaminant concentration and hydraulic conductivity within said control plan using said conditional probability distributions,
    d) generating realizations of spatial distribution of local mass flux within said control plane using said generated realizations of contaminant concentrations and hydraulic conductivity, and
    e) estimating a probability distribution of mass discharge within said control plane using said generated realizations of local mass flux.

6. The method of claim 1, wherein said membership functions calculated are as follows:

$$d_i^k = \frac{x_i^k}{x_i^*} \; \{X_i^k, d_i^k\} \; i = 1, \ldots, n \; k = 1, \ldots, m$$

where m is the total number of said candidate sampling locations, n is the number of criteria, $d_i^k$ is a membership function scaling the value into the interval [0, 1] using the maximum value of $X_i^k$, $X_i^*$ is the highest conditional variance among m locations.

7. The method of claim 1, wherein said compromise solution is calculated as follows:

$$L_1(\lambda, k) = 1 - (\lambda_1 d_1^k + \lambda_2 d_2^k).$$

8. The method of claim 1, further comprising the step of displaying said accuracy plot of said probability distribution of mass discharge using said computer.

9. The method of claim 1, further comprising the step of collecting samples using a drilling or sampling system.

* * * * *

UNITED STATES PATENT AND TRADEMARK OFFICE
CERTIFICATE OF CORRECTION

| | | |
|---|---|---|
| PATENT NO. | : 8,615,379 B2 | Page 1 of 1 |
| APPLICATION NO. | : 12/518333 | |
| DATED | : December 24, 2013 | |
| INVENTOR(S) | : Ke Betty Li and Linda M. Abriola | |

It is certified that error appears in the above-identified patent and that said Letters Patent is hereby corrected as shown below:

On the Title page, item (54) and in the Specification, Column 1, the title should read "METHOD FOR MULTI-STAGE SPATIAL SAMPLING WITH MULTIPLE CRITERIA"

Signed and Sealed this
Twenty-fifth Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,615,379 B2                                           Page 1 of 1
APPLICATION NO.   : 12/518333
DATED             : December 24, 2013
INVENTOR(S)       : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 911 days.

Signed and Sealed this

Twenty-second Day of September, 2015

Michelle K. Lee
*Director of the United States Patent and Trademark Office*